(12) United States Patent  
Warner et al.

(10) Patent No.: US 8,554,311 B2  
(45) Date of Patent: Oct. 8, 2013

(54) SYSTEM AND METHOD OF NOISE REDUCTION IN AN ELECTROCARDIOLOGY STUDY

(75) Inventors: Adrian F. Warner, Wauwatosa, WI (US); Daniel R. Schneidewend, Wauwatosa, WI (US); Claudio P. Mejia, Wauwatosa, WI (US); Timothy P. Stiemke, Wauwatosa, WI (US); Rodger F. Schmit, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 23 days.

(21) Appl. No.: 13/248,892

(22) Filed: Sep. 29, 2011

(65) Prior Publication Data

US 2012/0323132 A1    Dec. 20, 2012

Related U.S. Application Data

(63) Continuation-in-part of application No. 13/162,838, filed on Jun. 17, 2011, now Pat. No. 8,515,530.

(51) Int. Cl.
*A61B 5/04* (2006.01)

(52) U.S. Cl.
USPC .......................................................... 600/509

(58) Field of Classification Search
USPC ................................................ 600/508–509
See application file for complete search history.

(56) References Cited

U.S. PATENT DOCUMENTS

| | | | |
|---|---|---|---|
| 4,420,815 | A | 12/1983 | Francis |
| 2008/0045832 | A1 | 2/2008 | McGrath |
| 2008/0315879 | A1 | 12/2008 | Saha |

FOREIGN PATENT DOCUMENTS

WO    99/04688 A1    2/1999

OTHER PUBLICATIONS

David W. Mortara. "Digital Filters for ECG Signals". pp. 511-514. http://www.mendeley.com/research/digital-filters-ecg-signals-11/.
Gholam-Hosseini et al., "EGC Noise Cancellation Using Digital Filters" Feb. 1998, 2nd International Conference on Bioelectromagnetism, pp. 151-152. http://www.mendeley.com/research/ecg-noise-cancellation-using-digital-filters-19/.
Widrow et al. "Adaptive Noise Cancelling: Principles and Applications". pp. 1692-1717. http://ieeexplore.ieee.org/xpl/freeabs_all.jsp?arnumber=1451965.
Search Report and Written Opinion from corresponding PCT Application No. PCT/US2012/053268 dated Nov. 29, 2012.
Webster, J., "The Electrocardiograph" Medical Instrumentation, Application and Design, Third Edition, 1998, John Wiley & Sons, Inc. New York, pp. 235-258.

*Primary Examiner* — Carl H Layno  
*Assistant Examiner* — Paula J Stice  
(74) *Attorney, Agent, or Firm* — Patrick J. Kim; William T. Kryger

(57) ABSTRACT

A system to use in combination with an ECG signal acquisition system connected to an arrangement of electrodes on a subject is provided. The system can include an antenna system in communication with the ECG signal acquisition system, a location tracking system operable to track a direction and a location of the antenna system relative to a reference, and an interface connected in communication with the ECG signal acquisition system and the location tracking system. The interface includes an output indicative of a direction of a source of the noise signal detected by the antenna system. A filter reduces an effect of the noise signal on an acquired ECG waveform data received by the ECG signal acquisition system.

13 Claims, 11 Drawing Sheets

SYSTEM AND METHOD OF NOISE REDUCTION IN AN ELECTROCARDIOLOGY STUDY

RELATED APPLICATIONS

This application is a continuation-in-part of U.S. Pat. No. 8,515,530 entitled "System and Method of Noise Detection in an Electrophysiology Study" filed on Jun. 17, 2011, and hereby claims priority to the above-identified patent application and herein incorporates by reference in its entirety.

FIELD OF USE

The subject matter generally relates to a system and method of noise reduction, and more particularly to a system and method of identifying and reducing noise attenuation in an electrocardiology study.

BACKGROUND

A setting, establishment and maintenance of a minimized noise levels in a work environment is a challenge and need of field engineers today. Examples of sources of noise interference can include ungrounded electrical extension chords, electrical sockets, equipment having a large electrical energy demand, etc. Such noise interference can often interfere with measurement and resolution of electrical signals taking place to conduct studies by processing equipment, or to test, debug, or maintain electrical signal processing equipment.

For example, one environment where noise is a concern can be in a healthcare setting where electrocardiology studies are taking place. Electrocardiogram (ECG) systems can measure small biopotential signals within a person's heart or at the surface of a person's skin. These biopotential signals can range as low as 100 uV, and can be resolvable to as little as 30 uV. For example, *Medical Instrumentation—Application and Method* by John G. Webster (1988) describes how electrodes can be located on a person (e.g., frontal plane or transverse plane) to track an ECG to be used as a diagnostic tool to examine functioning of the heart.

There is a need for an environment for processing equipment having minimized noise levels that can enhance electrical signal processing performance.

BRIEF SUMMARY

There is a need or desire a system and method to locate sources of environmental noise that can interfere with measurement and resolution of electrical signals taking place to conduct studies by electrical signal processing equipment, and furthermore to automatically identify a filter to reduce the effects of the environmental noise. The above-mentioned drawbacks and needs are addressed by the embodiments described herein in the following description.

According to one embodiment, a system to use in combination with an ECG signal acquisition system connected to an arrangement of electrodes on a subject is provided. The system can include an antenna system in communication with the ECG signal acquisition system, a location tracking system operable to track a direction and a location of the antenna system relative to a reference, and an interface connected in communication with the ECG signal acquisition system and the location tracking system. The interface can include an output indicative of a direction of a source of the noise signal detected by the antenna system. A filter can reduce an effect of the noise signal on an acquired ECG waveform data received by the ECG signal acquisition system.

According to another embodiment of the subject matter described herein, a method of acquisition of an ECG waveform data from a subject with an ECG image acquisition system having at least one electrode attached at the subject is provided. The method can comprise the steps of sampling the noise signal detected by the antenna system; automatically detecting a direction of the source of noise relative to an alignment of the subject; and automatically calculating a nearest electrode from the plurality of electrodes that is proximate to the direction of the source of noise signal and a filter to reduce attenuation to the ECG waveform data caused by the source of noise signal.

Systems, methods, and computer program products of varying scope are described herein. In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
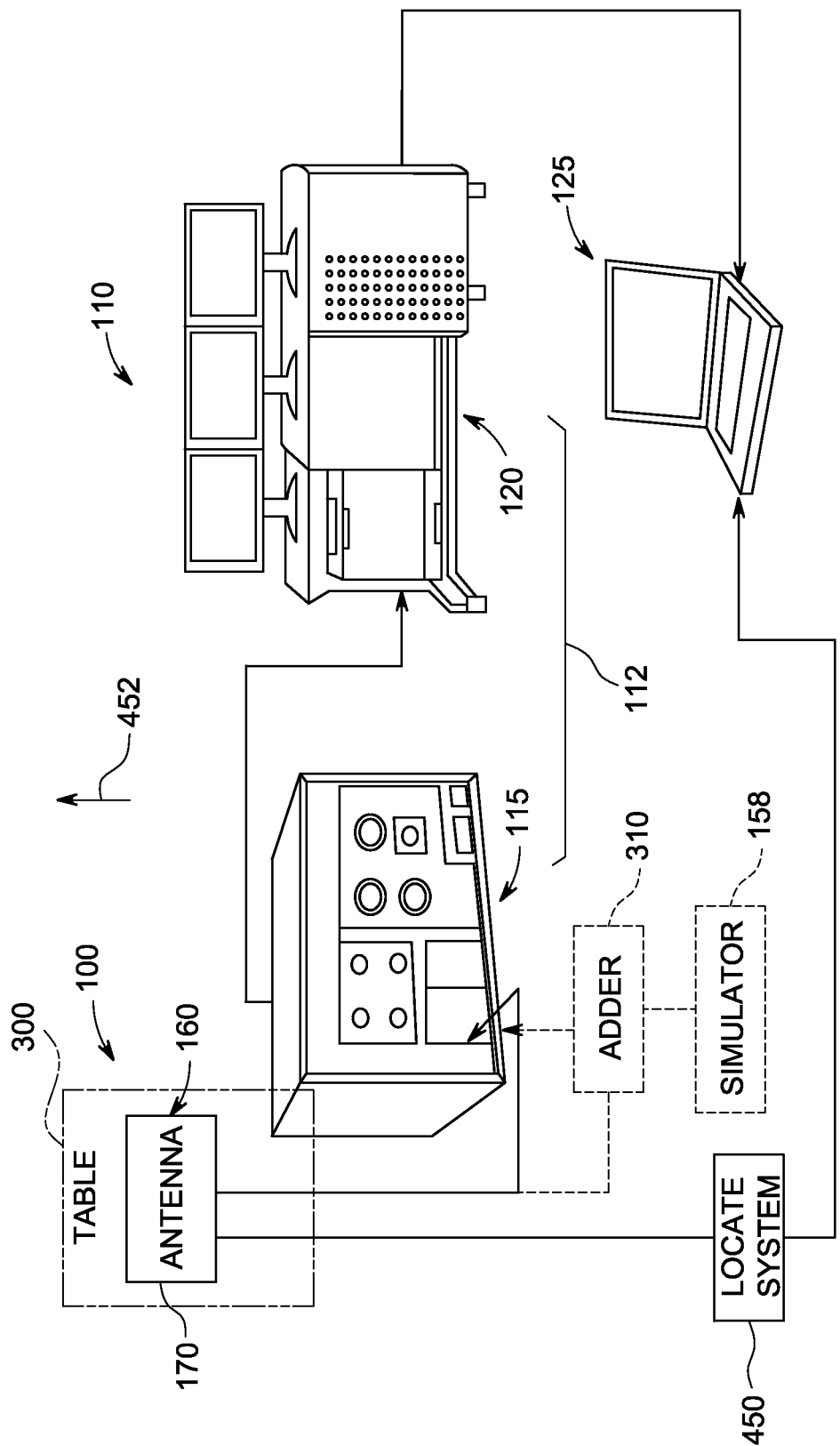
FIG. 1 shows a schematic diagram of an embodiment of a system operable to enhance detection, direction, and isolation of sources of noise interference in an electrical signal processing environment in accordance with the subject matter described herein.

FIG. 1 illustrates one embodiment of a system 100 operable to enhance detection, direction, and isolation of sources of noise interference in an electrical signal processing environment. An example of the electrical signal processing environment can be a biopotential study room where a subject 105 (e.g., person or animal) can undergo a study by a biopotential signal acquisition system 110. One example of the biopotential signal acquisition system 110 includes an electrocardiogram (ECG) signal acquisition system (surface or intracardiac) 112 as shown. Yet, other examples of types of biopotential signal monitoring systems can include but is not limited to systems for measurement of an electro encephalogram (EEG), electroneurogram (ENG), electromyogram (EMG), and electroretinogram (ERG) of a subject 105 (e.g., human or animal). Examples of sources of noise interference can include, but is certainly not limited to, ungrounded electrical extension cords, electrical sockets, high-energy consumption equipment, etc. The system 100 in combination with an ECG signal acquisition system 112 can be applied to various ECG signal acquisition applications such as stress test ECG, resting ECG, exercise ECG, patient monitoring, fibrilators, etc. involving sensitive electrical signal recording and processing.

For sake of example, the following description is of the ECG signal acquisition system 112 of the subject matter described herein can include wired or wireless communication of an amplifier 115, a recorder 120, and a series of electrodes 130 located at the subject 105. Yet, the recorder 120 is not required. The ECG signal acquisition system 112 can be connected in wired or wireless communication with an interface 125 of the system 100.

Examples of the biopotential signal acquisition systems 110 can be a Mac 3500, Mac 5500, Mac 400, CARDIOLAB™ EP Recorder, MAC 1600 ECG Monitor or the Solar 8000i Patient Monitor produced by GE™ Healthcare; the ELI 350 or X-Scribe produced by Mortara Instrument; the Burdick 8500 or Quniton Eclipse or Q9550 produced by Cardiac Science; the EP-Workmate Recording System produced by St. Jude; a GY Electrophysiology/EP recorder system produced by Henan Huanan Medical Science and Technology Co. Ltd.; the AXIOM SENSIS XP Hemo/EP recorder produced by SIEMENS™; the CARTO XP and CARTO 3 Mapping systems produced by BIOSENSE WEBSTER™; the Lab System Pro produced by BARD™ Electrophysiology; the Pagewriter TC30, TC50 or TC70, the IntelliVue MP40, MP50, MP60 and MP70, or the HeartStart MRx Monitor/Defibrillator produced by PHILIPS™; the 1500 Patient Monitor produced by Welch Allyn; or the Physio Control Lifepak 12 produced by MEDTRONIC™.

The electrodes 130 can be generally in contact with or coupled at a skin surface of the subject 105 and operable to acquire the ECG signals associated with cardiac activity of the subject 105. Each electrode 130 can be electrically connected to transmit the acquired ECG signals via a lead wire 135 to the amplifier 115. A known distribution of electrodes on the subject 105 can include right arm electrode 140, a left arm electrode 145, a right leg electrode 150, a central electrode 152, and a left leg electrode 155. Examples of the electrodes 130 can also be located internally either adjacent or at the heart of the subject 105.

The amplifier 115 can generally operate to receive input of the ECG signal, translate the ECG signal from analog to digital, increase the signal strength while maintaining high fidelity, and transmit the digitized ECG signal to the recorder 120 for further signal processing. The recorder 120 can generally perform signal processing for display and storage of the acquired ECG signal.

In another embodiment of the system 110, the amplifier 115 can be connected in communication to receive ECG signals transmitted from an ECG simulator 158 operable to recreate or simulate an ECG signal otherwise acquired from electrodes 130 on the subject 105. An example of the ECG Signal simulator 158 is produced by GE Healthcare, or the Multiparameter Patient ECG Simulator produced by the Fluke Corporation.

Figure 2:
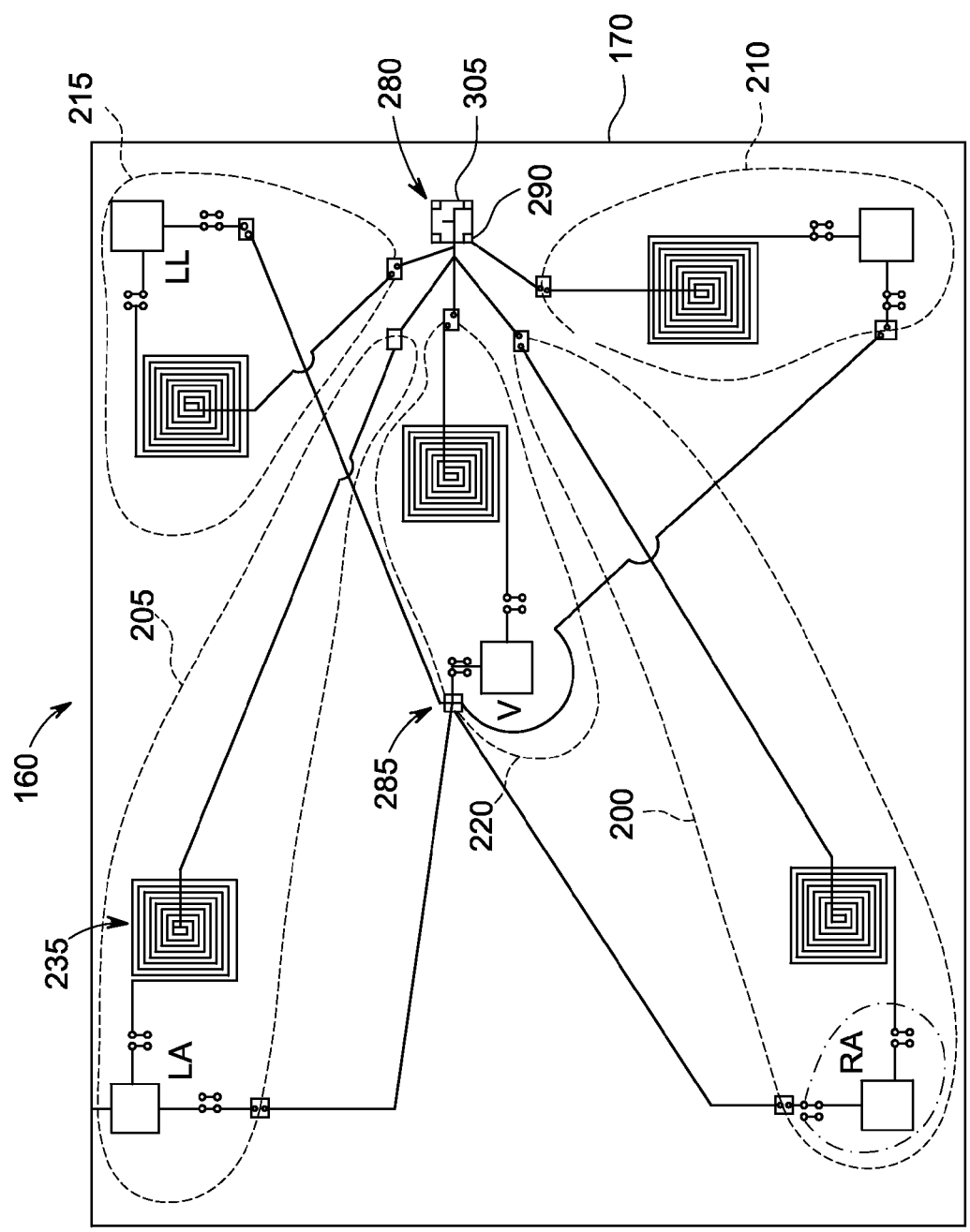
FIG. 2 shows a schematic diagram of one embodiment of an antenna system having an arrangement of electrical sub-circuits on a circuit board to detect noise attenuation experienced by electrodes in acquisition of a biopotential signals emitted from a patient in accordance with the subject matter described herein.

Referring to FIG. 2, the system 100 can generally include an antenna system 160 electrically connected in communication with the amplifier 115 (See FIG. 1). An embodiment of the antenna system 160 can generally include an electrical circuit board 170 comprised of an electrical insulating substrate material configured to be mounted with or receive electrical subcircuits comprised of metallic etchings. The electrical circuit board 170 can be rectangular shaped and sized generally to be proportional to an average size of a person's torso 175. The dimensions and shape (e.g., polygon, circular, or combination thereof) of the electrical circuit board 170 can vary to accommodate for other physiological or environmental factors.

Still referring to FIG. 2, the antenna system 160 can further include a series of electrical subcircuits (described below) mounted on the circuit board 170 having objects or components that, solely or in combination, correlate to or operate as a proxy for the attachment of electrodes 130 and lead wires 135 leading from the subject 105 to the amplifier 115 in acquisition of an electrocardiogram signal from the subject 105.

An embodiment of the series of electrical subcircuits can generally correlate to a known topology or method (e.g., augmented leads in the frontal plane, precordial leads in the transverse plane) to place the electrodes 130 on the subject 105 so as to acquire the ECG signal. In one such example, the antenna system 160 can include first or right arm electrical subcircuit 200 that correlates to the electrode and lead wire 135 leading from the right arm (RA) of the subject 105, a second or left arm electrical subcircuit 205 that correlates to the electrode and lead wire leading from the left arm (LA) of the subject 105, a third or right leg electrical subcircuit 210 that correlates to the electrode and lead wire leading from the right leg (RL) of the subject 105, a fourth or left leg electrical subcircuit 215 that correlates to the electrode and lead wire leading from the left leg (LL) of the subject 105, and fifth or central terminal electrical subcircuit 220 that correlates to a central terminal (CT) as a point to measure an average of the acquired signals detected at the other three electrodes RA, LA and LL. The third electrical subcircuit 210 can be treated as a reference (e.g., electrical ground) to measure the electrical potential with respect to the signals acquired and detected at the first, second, and fourth electrical circuits 200, 205, 215 in an analogous manner as to how the RL electrode 150 can be used in tracking and performing a frontal plane ECG study.

Each of the electrical subcircuits 200, 205, 210, 215, 220 can include etched objects (described below) that in combination are configured to correlate to and have substantially (e.g., within twenty percent of a standardized electrical model of the patient electrode equivalent circuit) the same electrical impedance (including resistance, inductance and capacitive effect) as the use of electrodes 130 and lead wires 135 leading from the subject 105 to the amplifier in use in detection or acquisition of biopotential signals from the subject 105.

Referring to FIG. 2, an embodiment of one or more of the electrical subcircuits 200, 205, 210, 215, and 220 can include a first circuit component or object that exhibits an impedance that correlates to the impedance of the electrode 130 attached at the person's skin surface. The first circuit component or object 230 can be a metallic composition (e.g., copper etching) of similar size, shape, dimensions or surface area to correlate to the conductance of the electrode 130 that attaches at the subject 105. An embodiment of the first object 230 can be rectangular shaped, but the size, shape, dimension or surface area of the first object 230 can vary.

One or more of the electrical subcircuits 200, 205, 210, 215, and 220 can further include a second circuit component or object 235 having an electrical impedance that correlates to the impedance associated with the electrode lead wire 135 connecting the amplifier 115 to the electrode 130 attached at the subject 105. An embodiment of the second object 235 can be of length substantially similar to a length of the electrode wire. The second object 235 can be a metallic etch having a length arranged in a coil shape on the circuit board 170. The shape of the metallic etch of the coil can be polygonal (e.g. shown as square) or circular or serpentine shape or other shape and is not limiting.

Figure 3:
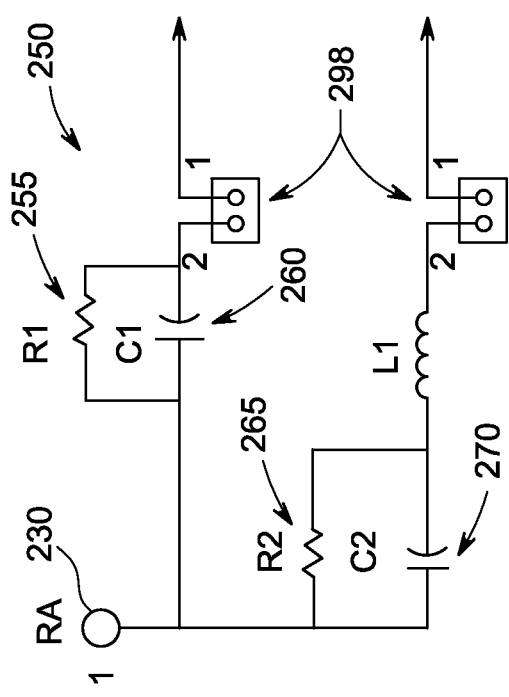
FIG. 3 illustrates a detailed schematic diagram of one embodiment of an electrical subcircuit to simulate an electrode located at a right arm in acquisition of biopotential signals from a patient in accordance with the subject matter described herein.

Referring to FIGS. 2 and 3, one or more of the electrical subcircuits 200, 205, 210, 215, and 220 can further include a subcircuit 250 comprising a first resistor 255 and capacitor 260 pair connected in electrical parallel connection and of electrical inductance and impedance value to correlate to the impedance (including resistance, capacitance, and inductance) associated with the impedance of the attachment of the electrode 130 to the skin or surface of the subject 105; and a second resistor 265 and capacitor 270 pair in electrical parallel connection to one another and of size such that the impedance can be substantially similar to an impedance of a bodily tissue that transmits electrical signals (e.g., associated with beating of the heart) through the subject 105. One embodiment of the impedance of the first resistor 255 and capacitor 260 pair can be of a threshold of an impedance value known in the industry associated with a poor attachment of the electrode 130 to the surface of the subject 105. Moreover, one embodiment of the thresholds of impedance of one or more of the subcircuits 200, 205, 210, 215, 220 can be of a value substantially equal to thresholds of published industry standards for impedance as defined for each correlative effect as defined herein.

Figure 4:
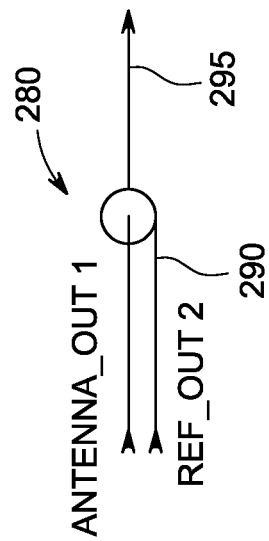
FIG. 4 illustrates a detailed schematic diagram of one embodiment of an antenna output of the antenna system of FIG. 3 in accordance with the subject matter described herein.

Referring to FIGS. 2, 3 and 4, an embodiment of the antenna system 160 can further include an electrical connection of an output from each of the first, second, third, fourth, and fifth electrical subcircuits 200, 205, 210, 215, and 220 to a combined antenna output connector 280 (See FIGS. 2 and 4) for communication to the amplifier 115. The antenna system 160 can further include an electrical connection of a common terminal 285 (See FIG. 2) from each of the first, second, third, fourth, and fifth electrical subcircuits 200, 205, 210, 215, 220 in electrical connection to one another. The fourth electrical subcircuit 215 can include a reference terminal connection to an electrical reference or an electrical ground terminal 290 (See FIGS. 2 and 4) at the combined antenna output connector 280. An embodiment of the combined antenna output connector 280 can be a Bayonet Neill-Concelman (BNC) connector configured to receive a connection from a coaxial cable 295 (See FIG. 4) to communicate the acquired antenna signals to the amplifier 115. Yet, the type of connector 280 and communication link (e.g., wireless, wired) can vary. The coaxial cable 295 can include an electrical shield to isolate and inhibit contamination of the electrical signal from the antenna system 160.

Each of the first, second, third, fourth and fifth electrical subcircuits 200, 205, 210, 215, and 220 can include a pair of electrical connector terminals 298 that isolate connection or disconnection of the respective electrical subcircuits 200, 205, 210, 215, and 220 with the remainder on the circuit board 170. Thereby, each subcircuit 200, 205, 210, 215, 220 can be designed to provide discrete signal output of measured noise interference from each subcircuit 200, 205, 210, 215, 220 for sequential or parallel communication for illustration to the user at the recorder 120 or interface 125.

Another embodiment of the antenna system 160 can further include a second substrate layer or insulating layer separating the first substrate layer and electrical subcircuits mounted thereon from an electrical conducting layer connected to an electrical ground 305.

According to one embodiment as illustrated in FIG. 1, the antenna system 160 can be coupled to or constructed integrally with a table 300 in support of the subject 105 during acquisition of the ECG signal. Yet, another embodiment of the antenna system 160 can be independently constructed to be uncoupled and mobile to move in isolation of the patient table 300.

In another embodiment of the antenna system 160, output from each of the electrical subcircuits 200, 205, 210, 215, 220 of the antenna system 160 can be electrically connected to a switch mechanism (not shown) so as to automatically isolate the electrical potential across selective pairs of electrical subcircuits 200, 205, 210, 215, 220 in a manner similar to isolation of electrical potential across the electrodes 130 in tracking an electrocardiogram of the patient 105.

Figure 5:
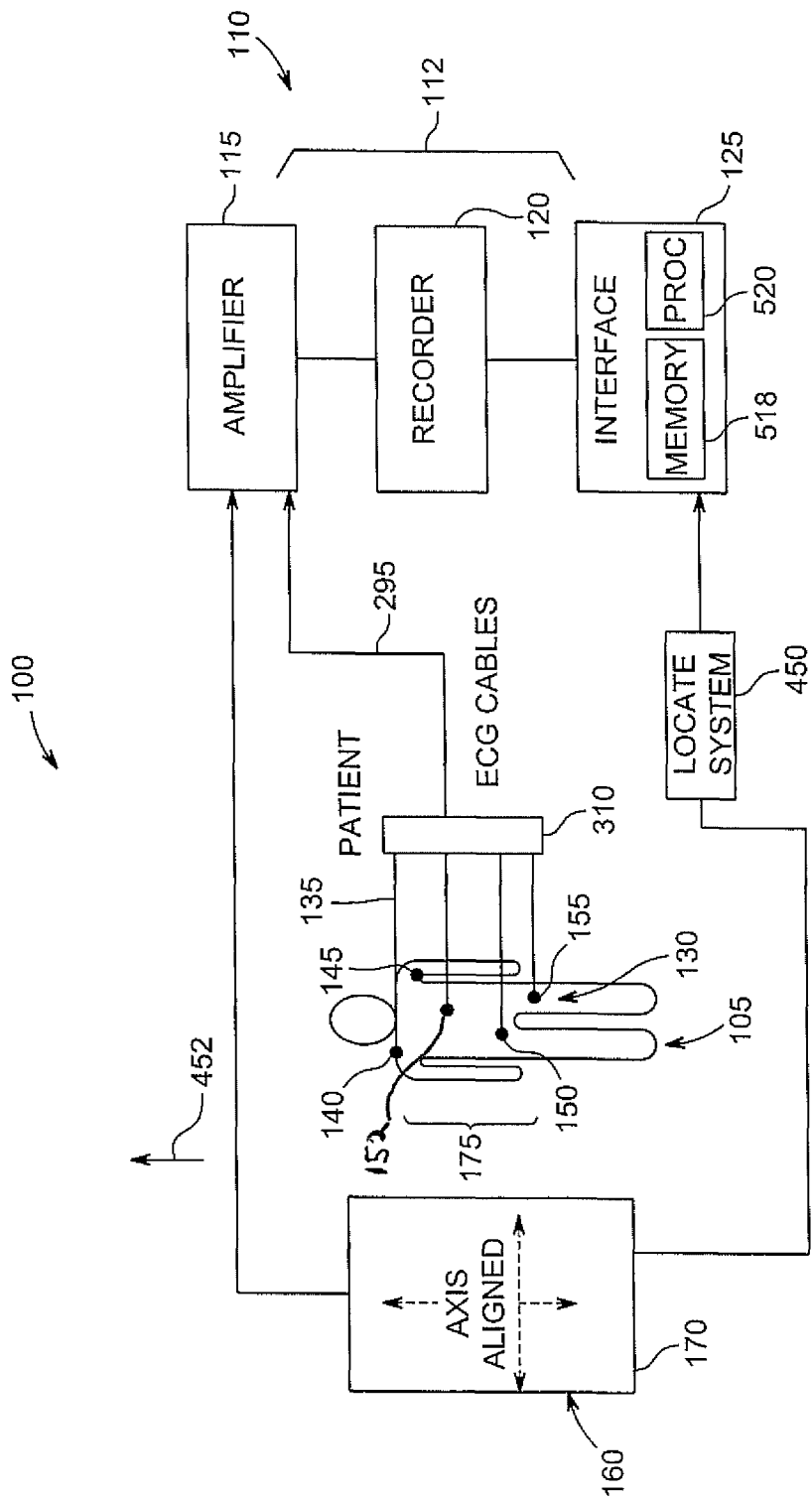
FIG. 5 shows a schematic diagram of an embodiment of the system of FIG. 1 operable to simulate acquisition and measurement of noise attenuation in a bipotential signal study of a patient in accordance with the subject matter described herein.

Referring to FIG. 5, the system 100 can further include the biopotential signal simulator 158 (e.g., ECG signal simulator) that, along with the electrical output line from the antenna system 160, can be in connected in communication with an adder or similar type of electrical signal mixing device 310 operable to selectively isolate or combine/mix one or more of the acquired signals from the simulator 158 and the antenna system 160 for communication to the amplifier 115 and recorder 120.

Referring to FIGS. 1 and 5, the interface 125 can be a laptop or general computer connected in communication with the ECG signal acquisition system 110, such as the recorder 120. The interface 125 can be operated by a field engineer or service technician working to diagnose and increase an operating efficiency of the ECG signal acquisition system 112, or identify sources of noise interference distorting the output from the ECG signal acquisition system 112.

Figure 6:
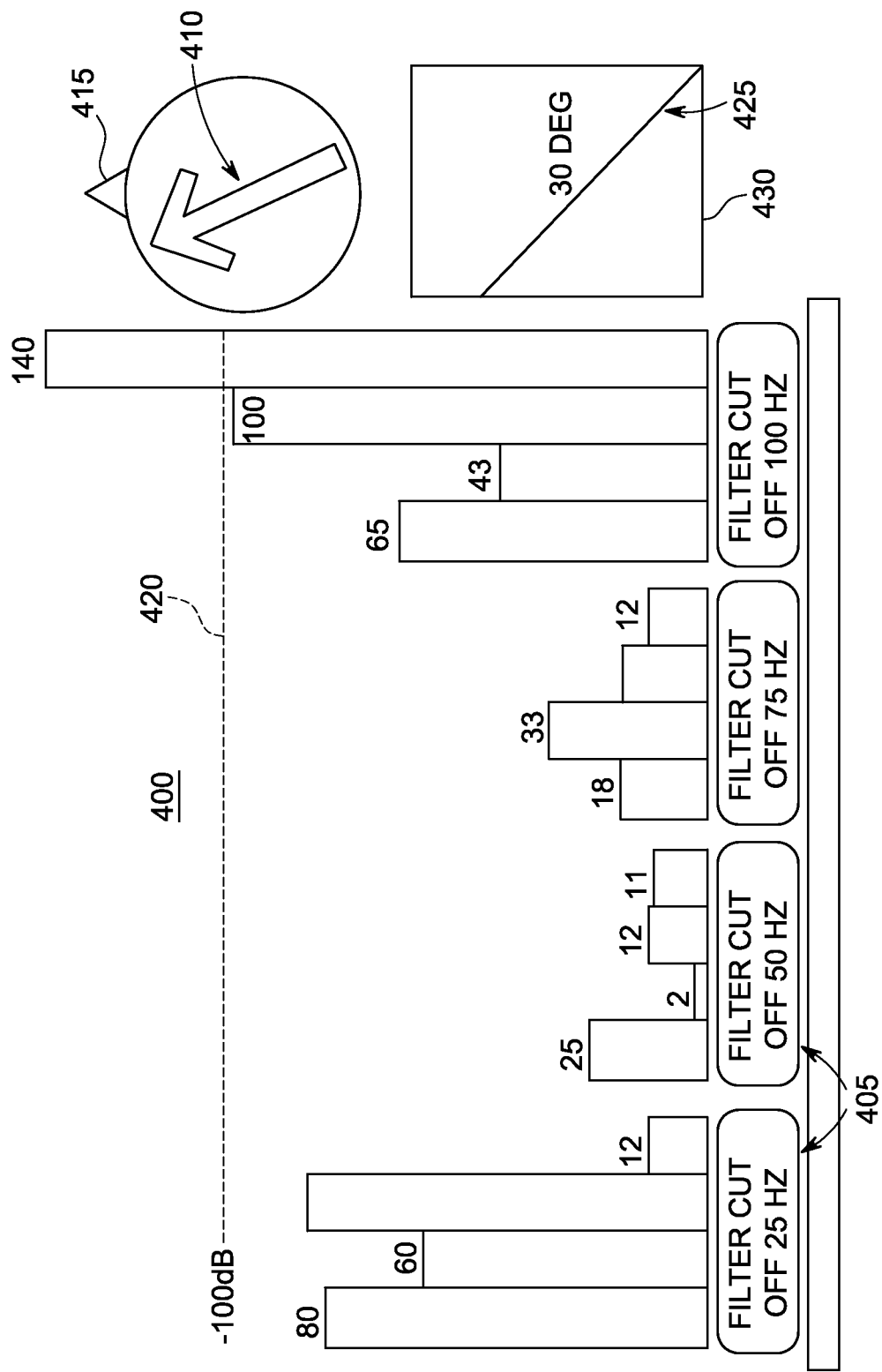
FIG. 6 shows an embodiment of a visual display output by the system of FIG. 1 in accordance with the subject matter described herein.

FIG. 6 illustrates an embodiment of a graphic display 400 generated by the system 100. The graphic display 400 can include graphic illustrations representative of a measure of different ranges or steps of filtration of cutoff frequencies 405 of the acquired electrical signals communicated from the antenna system 160 and/or simulator 158 for illustration at the ECG signal acquisition system 112 or at the interface 125 or both. The number of cutoff frequencies or ranges of filtration can vary and is not limiting on the subject matter described herein. The graphic display 400 can further include graphic illustrations representative of an orientation or direction of an alignment 410 of the circuit board 170 and mounted electrical subcircuits relative to a reference (e.g., alignment of the patient table 300 in a horizontal plane) 415 on the display 400. By rotating the circuit board 170 until detecting and measuring the largest intensity or amplitude 420 of electrical signals in the filtration or cutoff frequency range of noise, an operator can observe the graphic illustration of an orientation or direction of alignment 410 of the circuit board 170 that can point the observer to the direction of each source of noise in the space that can affect the results of ECG signal acquisition performed on the subject 105. The graphic display 400 can further include a visual graphic of a direction or orientation 425 of the circuit board 170 in the vertical direction relative to a reference (e.g., reference can be height level of the patient table 300) 430 on the display 400.

Referring to FIGS. 1 and 5, the system 100 can further include a location or tracking system 450 operable to track the location (e.g., rectangular x,y or x, y, z coordinates, latitude, longitude, height, etc.) and orientation (e.g., 180 or 360 degree angular alignment) of the antenna system 160 relative to a physical reference 452 of the space. Thereby, the tracking system 450 can support generation of the visual graphics 410 and 425 described above. The location system 450 can employ various types of known location tracking technologies (e.g., accelerometers, gyroscopes, cameras, RFID, ultrasound, electromagnetic, infrared, optical scanners, etc.) and is not limiting on the subject matter described herein. The location system 450 can communicate this location and orientation information of the antenna system 160 relative to the physical reference 452 in the defined space for illustration at the interface 125 to the user. Thereby, the system 100 can illustrate detection of the source of the noise interference signal, with processing of the acquired ECG signals by the ECG monitoring system 112, relative to the reference 452 of the defined space as multiple graphic illustrations of a scalar, vector, or tensor representative of the amplitude in combination with the orientation and/or direction of each unique (e.g., frequency, wavelength, amplitude) noise interference signal. The antenna system 160 can be connected to communicate the noise interference signal to the ECG monitoring system 112 for communication at the interface 125. The location system 450 can be connected (e.g., wired or wireless) to communicate the orientation and location of the antenna system (e.g., the location and orientation of the circuit board 170) for combined illustration at the interface 125 of the largest amplitude 420 electrical signals in the cutoff frequency range of noise in combination with the orientation and location of the antenna system 160 with movement of the antenna system 160 in the defined space relative to the reference 452. Thereby, with movement of the antenna system 160 throughout the defined, the system 100 can illustrate via the interface 125 the detection and measure of the greatest noise interference signal within a defined bandwidth in combination with the location and orientation of the antenna system 160 (e.g., the circuit board 170) in general real-time with the detection and measurement of the noise interference signal.

Having generally provided the above-description of a construction of the embodiments the system 100 of the subject matter described herein, the following is a general description of embodiment of methods 505, 510, 515 of operating the embodiment of the system 100 described above. It should also be understood that the sequence or succession of the acts or steps of the method as described in the foregoing description can vary. Also, it should be understood that the methods 505, 510, 515 may not require each act or step in the foregoing description, or may include additional acts or steps not disclosed herein. One or more of following steps and acts of the methods 505, 510, 515 can also be in the form of computer-readable program instructions stored in memory 518 for execution by a processor or other computer programmable device 520 either of the interface 125 or in communication therewith.

Assume that an ECG recorder 120 is coupled in communication with the amplifier 115 in an ECG study room or defined space. The method of operation includes connecting the ECG simulator 158 and the antenna system in communication with the adder 310, and connecting the adder 310 in communication to the amplifier 115 and recorder 120. Also assume that the interface 125 can be connected in communication to receive the data communicated to the recorder 120.

Figure 7:
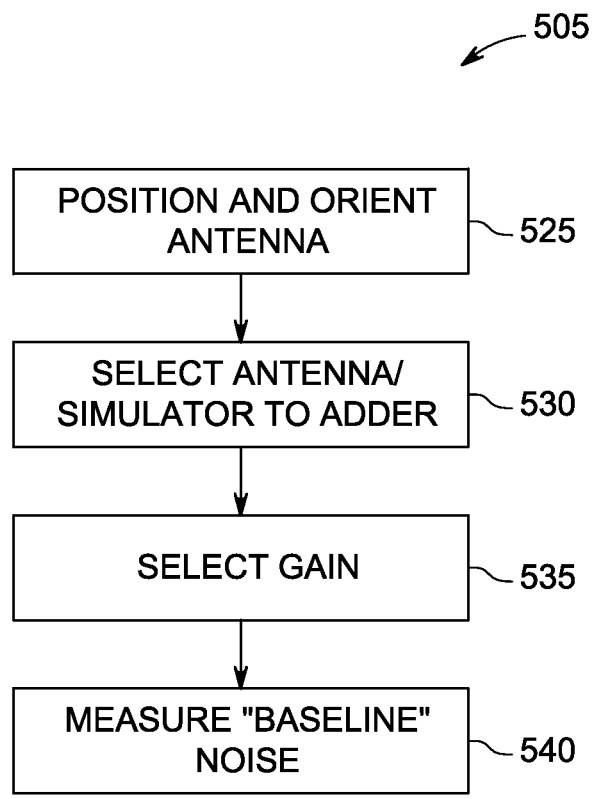
FIG. 7 shows a flow diagram of an embodiment of a method of acquiring a baseline noise measurement using the system of FIG. 1.

FIG. 7 shows an embodiment of the method 505 of acquiring a baseline noise measurement using the system 100 described above. Step 525 includes positioning or orienting the antenna system 160 in correlation to a position or orientation of the subject 105 to undergo the biopotential study. Step 530 includes connecting the antenna system 160 and the simulator in communication with the adder 310. Step 535 includes selecting at the adder 310 to receive only the signal communicated from the ECG simulator 158, and selecting desired amplifier gain setting to display simulator signal at the interface 125. Step 540 includes measuring and recording a baseline noise of within the system 100 for illustration at the display 400.

Figure 8:
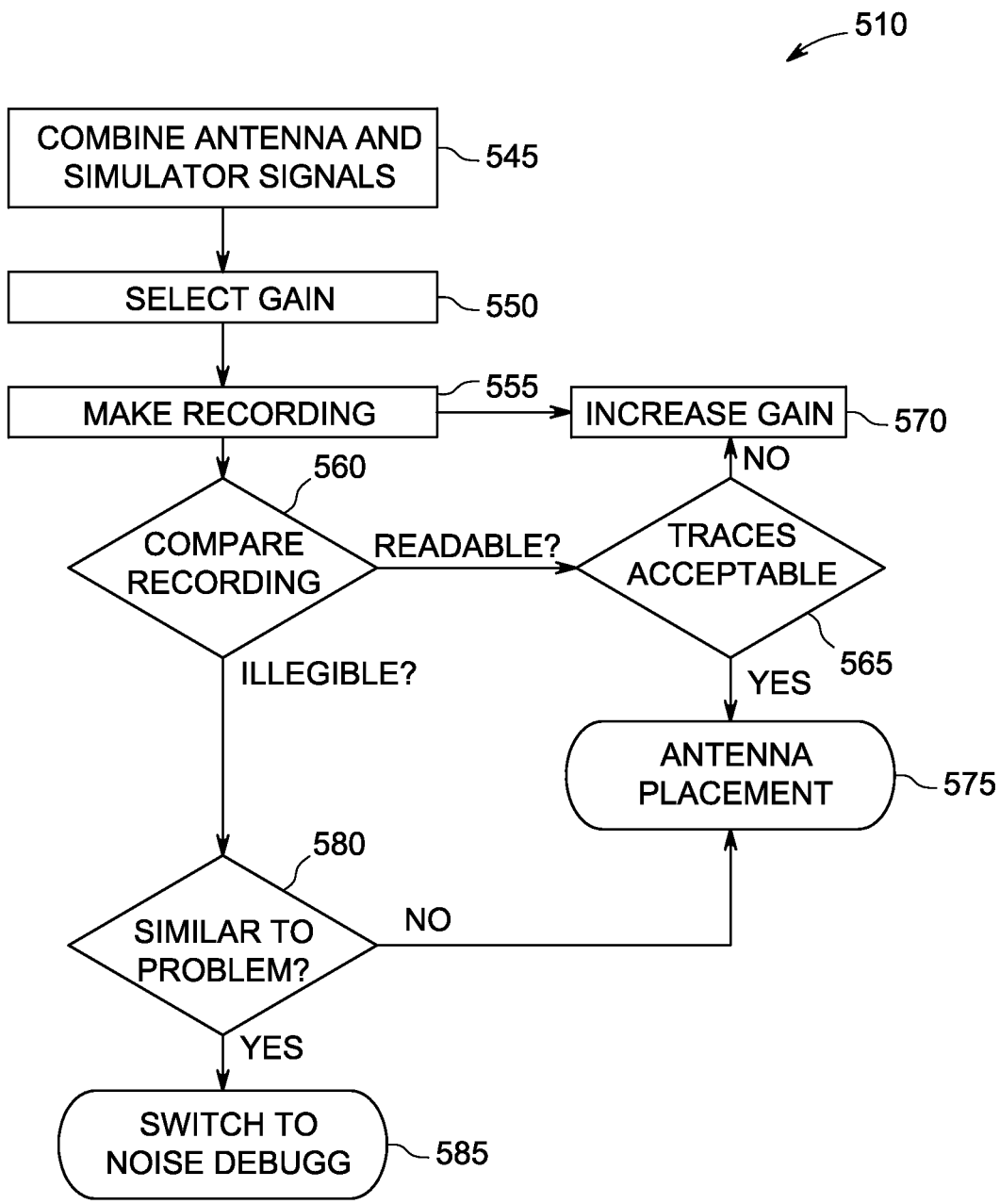
FIG. 8 shows a flow diagram of an embodiment of a method of performing noise simulation using the system of FIG. 1.

FIG. 8 shows an embodiment of the method 510 of performing a noise simulation. Step 545 includes switching the adder 310 to communicate a combined signal from the signals received from the simulator 158 and the antenna system 160. Step 550 includes selecting a gain at the recorder 120 to display the combined signal from the adder 310. Step 555 includes receiving an instruction to make a recording of the combined signal for illustration at the interface 125. Step 560 includes comparing the recording to a known problem signal or report for encountered noise in electrical signal processing, and receiving an instruction if the combined signal is readable or illegible. Step 565 includes receiving an instruction whether the recording of the combined signal is acceptable. If the instruction indicates not readable, Step 570 includes increasing the setting for the gain at the recorder 120 and returning to step 555. If the instruction indicates acceptable, step 575 includes placement and recording location of the circuit board of the antenna system 160. Step 580 includes comparing the recorded combined signal to the known problem signal or report. If receiving an instruction that the recorded combined signal is substantially similar to the problem signal or report, Step 585 includes switching or start of the method 515 described in FIG. 9. If receiving an instruction that the recorded combined signal is not substantially similar to the problem signal or report, then returning to step 575.

Figure 9:
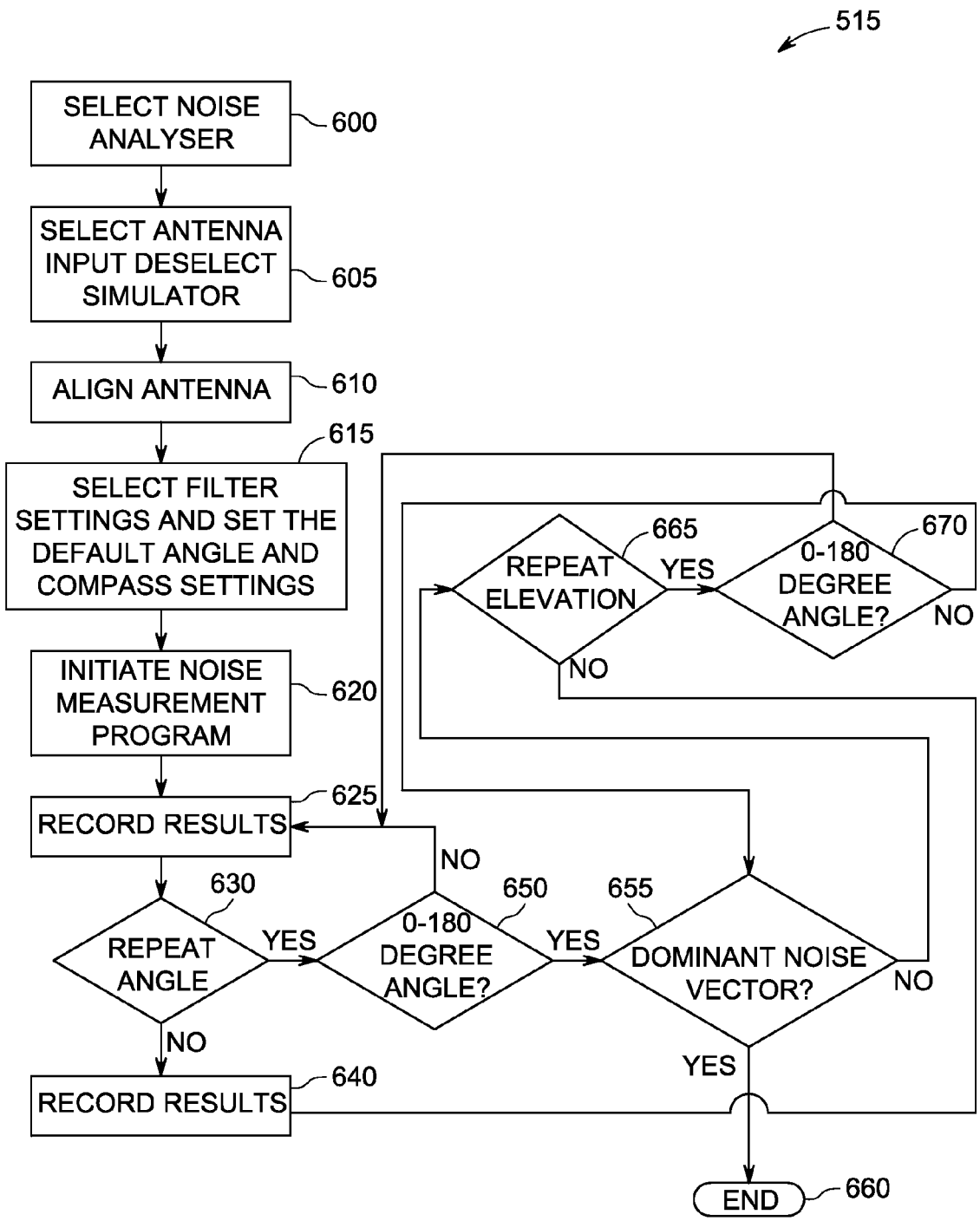
FIG. 9 shows a flow diagram of an embodiment of a method of performing noise angulation using the system of FIG. 1.

Referring now to FIG. 9 and the embodiment of the method 515 of performing noise debugging. Step 600 includes receiving an instruction of selection of noise analyzer functionality via the interface 125. Step 605 includes selecting to communicate the signal from the antenna system 160 only from the adder 310, and deselecting addition of the signal from the ECG simulator 158. Step 610 includes locating the circuit board 170 of the antenna system 160 in general alignment with orientation and location of the subject 105 to undergo the biopotential study. Step 615 includes receiving instructions of selected filter ranges, and a set default angle and compass setting. Step 620 includes receiving an instruction to record the signal from the antenna system 160 at the recorder 120. Step 625 includes receiving an instruction to record the signal analysis for illustration on the display 400. Step 630 includes receiving an instruction indicative to change an angle or orientation of the circuit board 170 of the antenna system 160, and returning to step 620. If receiving an instruction of no further orientation changes to the location or angular alignment or orientation of the circuit board 170, then step 640 includes recording the results of the signal analysis on the display and returning to step 610. If receiving an instruction to change the orientation of the circuit board 170 of the antenna system 160 and performing signal analysis on the signal from the circuit board 170, step 650 includes measuring a change of orientation of the circuit board 170 relative the reference for illustration on the display 400. Step 655 includes detecting if the current orientation of the circuit board 170 relative to the reference creates largest or dominant noise vector compared to analysis of signals for other orientations of the circuit board 170. If the dominant noise vector, step 660 is the end of the method. If not the dominant noise vector, step 665 includes recording a change in elevation of the circuit board 170 relative to the reference and proceeding to step 640 to record the results of the signal analysis in the display 400. Step 670 includes recording a change in orientation of the circuit board 170 in a vertical plane relative to a reference, and proceeding to step 640 to record the results of the signal analysis in the display 400.

Referring back to FIG. 5, the antenna system 160 can used in combination with the ECG acquisition system 112 in acquisition of the ECG waveform from the subject 105. Assume for sake of example that the antenna system 160 can be employed in combination with the ECG signal acquisition system 112 in a certain ECG signal acquisition application, such as stress test ECG, resting ECG, exercise ECG, patient monitoring, fibrilators, etc. involving sensitive electrical signal recording and processing. The ECG signal acquisition system 112 can include wired or wireless communication of the amplifier 115, the recorder 120, and the series of electrodes 130 located at the subject 105. The ECG signal acquisition system 112 can be connected in communication with the interface 125. The electrodes 130 can be generally in contact with or coupled at a skin surface of the subject 105 and operable to acquire the ECG signals associated with cardiac activity of the subject 105. Each electrode 130 can be electrically connected to transmit the acquired ECG signals via lead wires 135 to the amplifier 115. The distribution of electrodes on the subject 105 can include right arm electrode 140, the left arm electrode 145, the right leg electrode 150, and the left leg electrode 155. Of course, it should be understood that the electrodes 130 could also be located internally either adjacent or at the heart of the subject 105 and is not limiting on the subject matter described herein.

The antenna system 160 can be operated to capture noise signals during acquisition of ECG signal via the electrodes 130 from the subject 105. The alignment of the antenna system 160 can located to the capture noise signals in parallel to alignment of the electrodes 130 located on the subject 105. The antenna system 160 can be embedded in the bed 300 supporting the subject 105, or embedded on the amplifier 115, or located on top of the subject 105 (e.g., the subject's chest). The noise or input signals captured by the antenna system 160 can be communicated to the amplifier 115 and recorder 120 or interface 125 for processing (e.g., star-delta ECG type????) and measure of the detected bandwidths, wavelengths, frequencies or amplitude or combination thereof for illustration at the interface 125. The recorder 125 or interface 125 can be operable to sample the captured signals by the antenna system 160 for analysis in combination with measurement of the location or alignment or combination thereof by the location system for illustration of a change in amplitude, bandwidth, wavelength, or frequency of captured noise signals in combination with the alignment or location of the antenna system 160 for illustration at the interface 125. Thereby, the system 100 can provide the above-described illustrations to locate a direction of a source of noise attenuation relative to alignment of the subject 105 during the ECG study.

Figure 10:
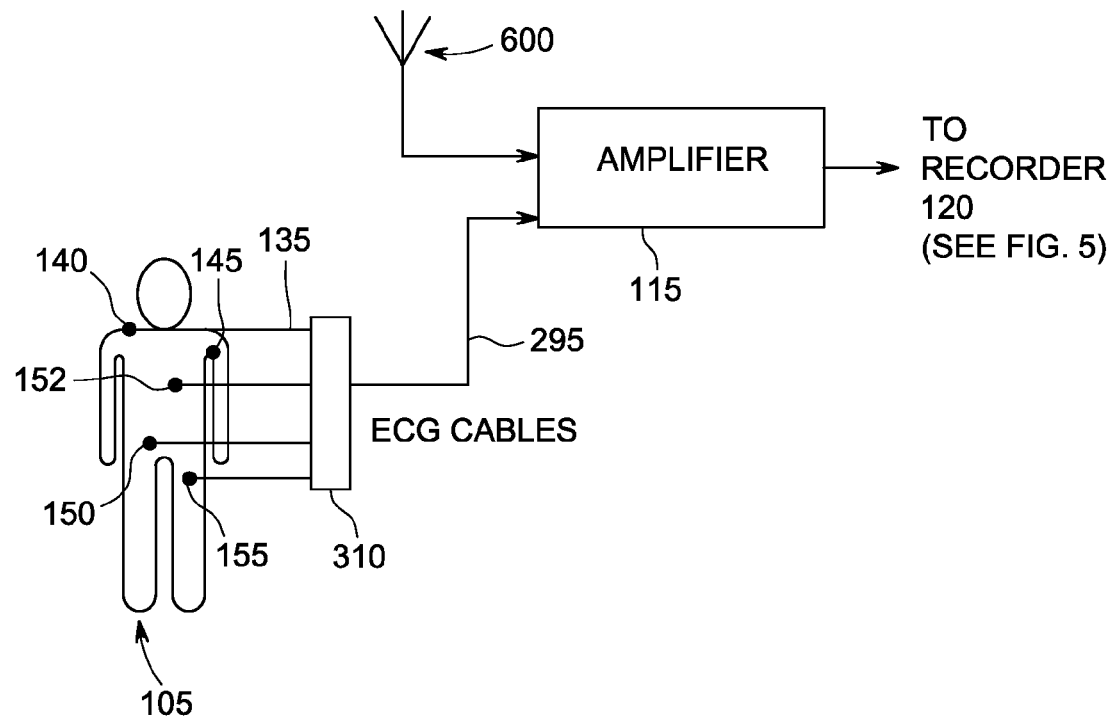
FIG. 10 shows a schematic diagram of another embodiment of a system operable to enhance detection, direction, and isolation of sources of noise interference in an ECG acquisition study in accordance with the subject matter described herein.

Although the subject matter described above is with respect to the embodiment of the antenna system 160, the subject matter is not so limited. FIG. 10 shows how the system 100 can include an antenna wire 680 connected to communicate captured noise signals in combination with acquisition of the ECG waveform of the subject 105 for communication to the amplifier 115 and then on to the recorder 120 (See FIG. 5) and interface 125 (See FIG. 5) for sampling and processing in a manner similar that described above.

Figure 11:
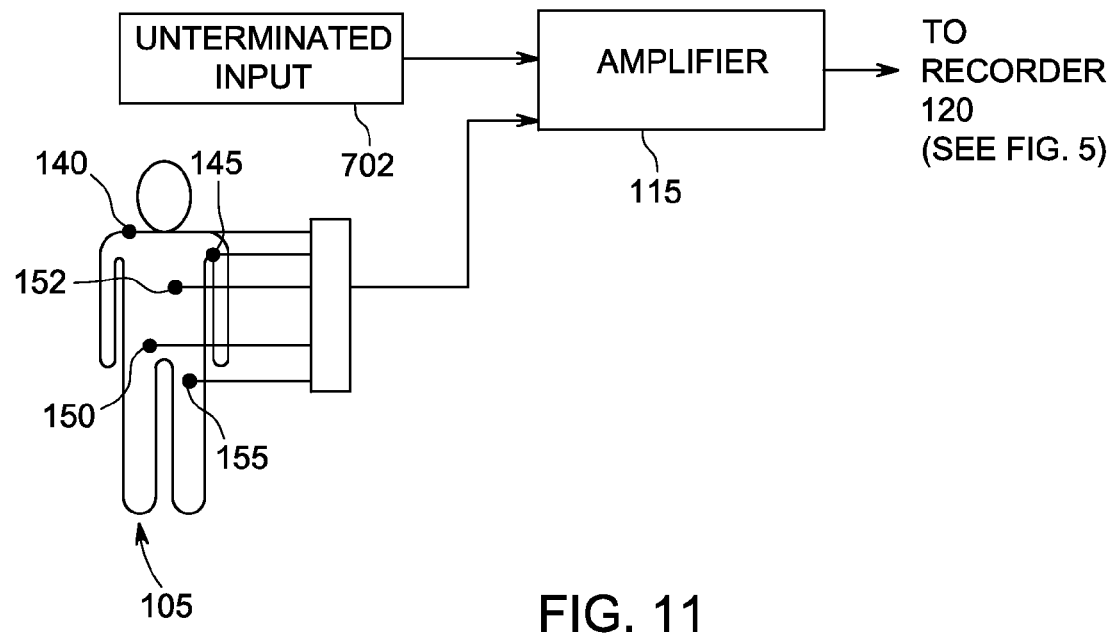
FIG. 11 shows a schematic diagram of another embodiment of a system, including an unterminated input connection at an amplifier of an ECG acquisition system, operable to enhance detection, direction, and isolation of sources of noise interference in an ECG acquisition study in accordance with the subject matter described herein.

According to another embodiment and referring to FIG. 11, the amplifier 115 can be configured to have an unterminated input or unterminated input connection 702. An examples of the unterminated input 702 can include one or more lead wires that extend from the amplifier 115 and located in alignment (e.g., in parallel to legs of subject) of the subject 105, but yet not connected to the subject 105. Another example of the unterminated input 702 can include an open circuit connection or channel of the amplifier 115. The unterminated input(s) 702 can also be a combination of the above-described examples. The captured noise signals at this unterminated input(s) 702 can be communicated to the recorder 120 or interface 125 for signal sampling and processing.

Figure 12:
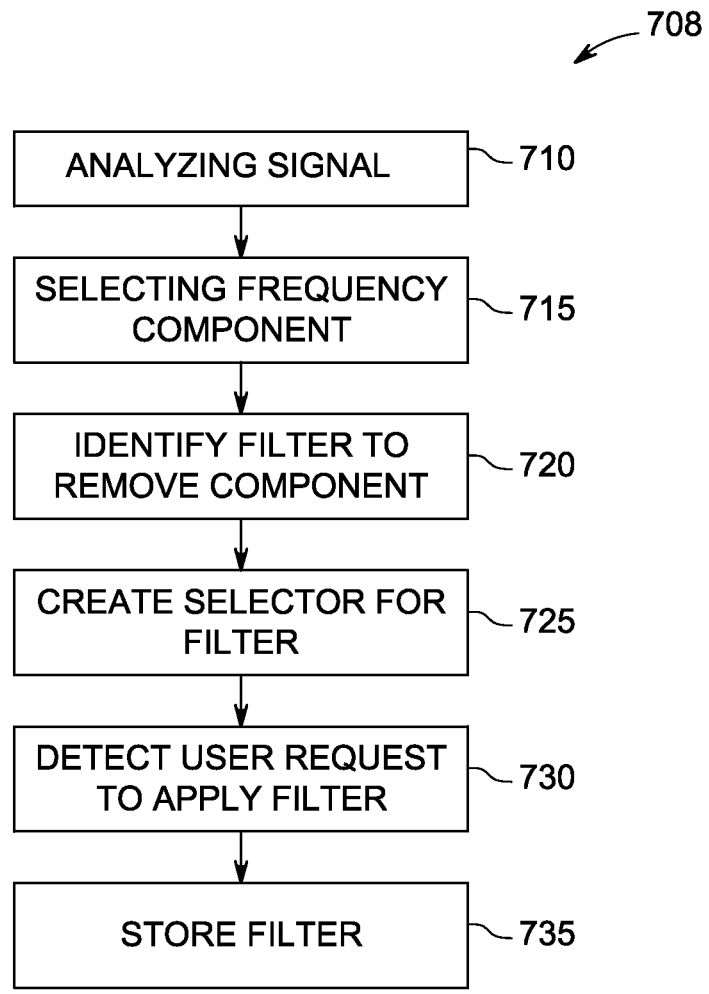
FIG. 12 illustrates a flow diagram of an embodiment of a method of creating and applying an adaptive filter using the system to enhance detection, direction and isolation of noise interference in accordance with the subject matter described herein.

Referring to FIG. 12, a method 708 of operating the system 100 in reducing noise attenuation on the acquired ECG waveform from the subject 105 can include program instructions on a data storage medium or memory 518 for execution by the processor 520. Step 710 can include sampling and analyzing the captured noise signals by the antenna system 160 or antenna wires or unterminated input as described above. For example with respect to each of a plurality (e.g., five) noise vectors run in a fast Fourier transform (FFT) analysis, step 710 can include capturing results for each noise vector by measuring dominant frequencies (e.g., identified by the central or center frequency) in the identified or predetermined noise environment.

Step 715 can include receiving instructions from the user or automatically selecting a frequency component of interest to direct applying one of a plurality of inverse transforms to the sampled signal so as to extract the noise signal or attenuation (associated with the selected frequency component) from the ECG waveform of the subject 105. Examples of the frequency component to select can be based on a measure of the dominant/highest amplitude or frequency, automatic selection, or receiving instructions from a selection from the user, for each periodic frequency component (e.g., identified by central frequency) in the range of noise. This step 715 can include automatically detecting a direction of the source of noise (e.g., direction of greatest amplitude per arrow in display) relative to the alignment of the subject 105, (per the direction automatically calculated and illustrated on the display). However, the step 715 can be performed on signals received via automatically identified or per instructions received for user selected channels, without applying the inverse transform to all of the channels connected to electrodes 130 connected at the subject 105, which may otherwise distort or unnecessarily condition captured ECG waveform data from electrodes 130 that are not substantially affected by the source of noise signal or attenuation.

Step 720 can include identifying one of a plurality of stored filters to remove the selected frequency component described in Step 715. Step 720 can include identifying or calculating a digital notch filter (e.g., adaptive or non-adaptive) to remove the measured noise frequencies in the acquired ECG waveform. Step 720 can include identifying the inverse transform to the captured subject ECG data delivered to one or more channels at the amplifier 115 connected to the respect electrode(s) 130 in the direction of the source of the noise signal. Step 720 can also include automatically calculating filter coefficient(s) for the filter (e.g., software or hardware) to be applied to the captured ECG waveform data from the subject so as to remove or decrease the effects of the frequency component associated with the detected noise signal or attenuation by the system 100. The identification and selection of the filter to apply to remove the frequency component can include a search of a library or database or look-up table based of particular frequency components (e.g., central or center frequency) and download the coefficients of a filter algorithm associated to remove the particular frequency components (e.g., associated with the respective central or central frequencies in the noise range or environment).

This step 720 can include performing a substantially real-time analysis to calculate the filter coefficient of an adaptive filter algorithm to remove the identified frequency component of the noise in the acquired ECG waveform data via one or more of the electrodes 130. Step 720 can include calculating a coefficient for creating multiple adaptive filter algorithm directed to condition or remove noise associated with multiple sources of the noise frequency component as detected by the system 100. For example, one adaptive filter can include an algorithm created and applied to reduce effects of noise from conventional alternating current (AC) frequencies, and another adaptive filter can include an algorithm created and applied to reduce effects of noise signal or attenuation associated with a motor controller in the area of the subject 105, and another adaptive filter can an algorithm created to reduced effects of noise from a nearby inductive load.

Step 725 can include creating a graphic representation of a selector on the user interface 125 operable to receive user instructions to apply one or more filters (e.g., static or adaptive) or combination thereof to the received ECG waveform data. The selector (see discussion below in regard to FIG. 13) can be labeled with the respective center or central frequency of the frequency component of the noise that the selector is intended to reduce or condition. This step can be performed to create multiple selectors.

Step 730 can include detecting or receiving instructions from the user via the graphic representation of the selector, to apply the filter described in step 720 to the acquired ECG waveform data received from one or more channels, per selection instructions received from the user. The above-described near real-time created and applied adaptive filters can be used in combination with one or more fixed filters previously stored in the system 100 or amplifier 115 or recorder 120 or interface 125 selected per instructions received from a user per input selection from a list (e.g., scroll down menu) of options at the interface 125.

Step 735 can include storing the filter (e.g., static or adaptive filter or combination thereof) in correlation to the graphic representation of the selector automatically created by the system 100, configured for later selection to apply to the acquired ECG waveform data from the subject 105 per instructions from the user.

The above-described method 708 can be described with reference to various types of filters (e.g., static, adaptive, subtractive, high or low band-pass, etc.) to condition or remove selected frequency components associated with noise attenuation included in the acquired ECG waveform data received via one or more channels of the ECG acquisition system. In another example of method 700, the filter applied can be a subtractive noise reduction type filter. Step 710 can include capturing an environmental noise signal or attenuation i.e., via the antenna system processed through lead forming network, for illustration on the graphic display channels at the interface 125. In response to receiving user instructions, the system 100 can be operable to calibrate the noise attenuation signal to match an amplitude-to-noise ratio picked up on the acquired ECG waveform data by inverting signals and maintaining 1:1 amplification, and applying a band pass filter to cut lower and upper frequency bands (such that inverted signal content can be passed without attenuation between these frequencies that can be selected via user instructions of lower or upper band pass filter limits or combination thereof, correct inverted signal time-delay to wanted signal sample time (e.g., to reduce associated phase error), and summing the inverted noise signal with the acquired ECG waveform data.

The above-described steps in method 708 can be repeated for each frequency component in the noise range to be removed from the acquired ECG waveform.

Figure 13:
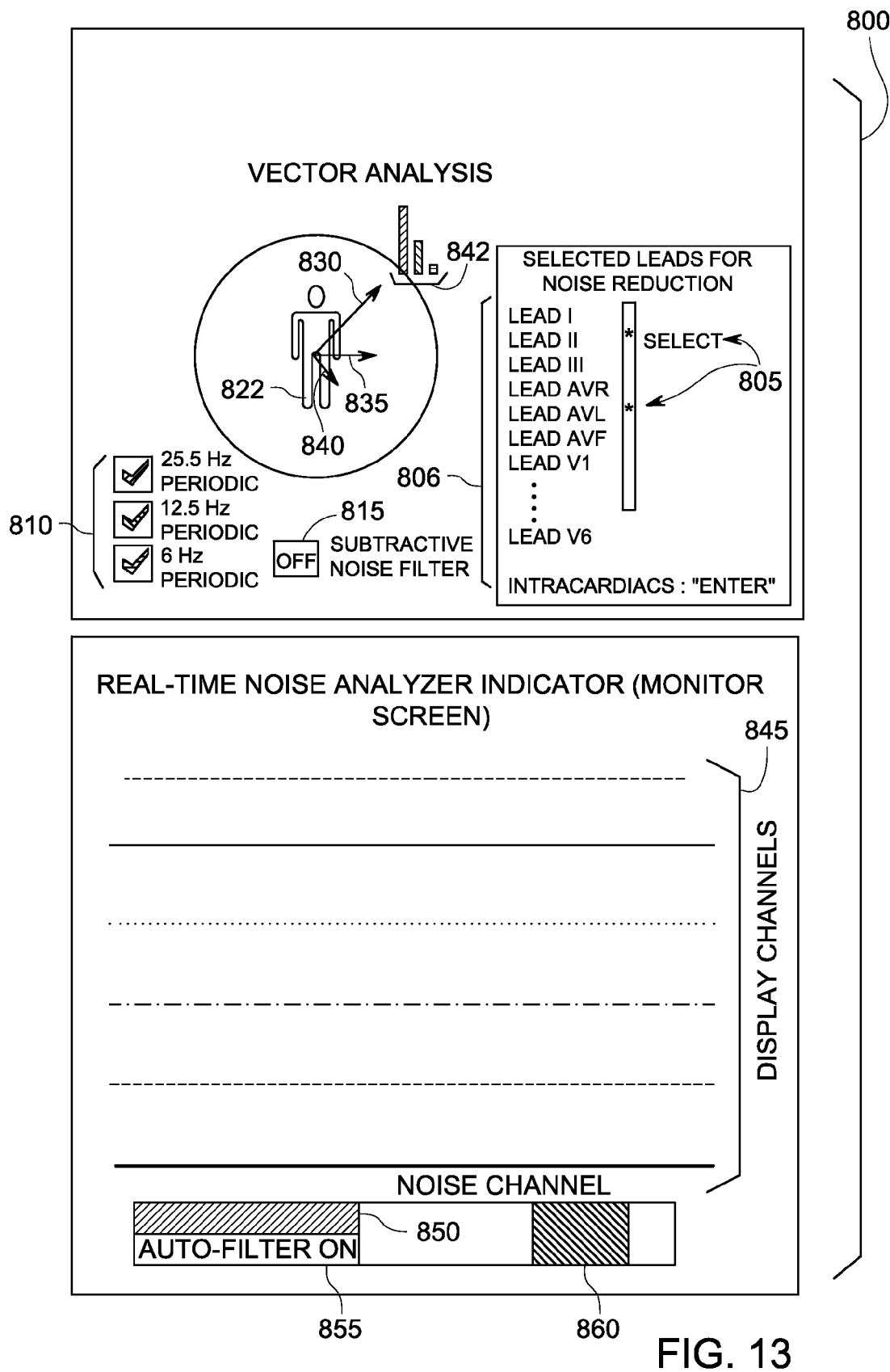
FIG. 13 illustrates a schematic diagram of an embodiment of an output display including visualization of an analysis of detection, direction and isolation of sources of noise interference in accordance with the subject matter described herein.

FIG. 13 illustrates an embodiment of a display 800 created at the interface 125 or at the recorder 120 by the system 100 in accordance to the subject matter described herein in removing or reducing effects of the noise attenuation or distortion associated with acquisition of ECG waveform via the recorder 120 from the subject 105. The display 800 can include a graphic illustration of an identifier of a unique adaptive filter 805 applied condition the ECG waveform data associated with a graphic illustration of the channel or lead or electrode 130 having a unique identifier 806 (external or intracardiac). The display 800 can include a graphic illustration of a unique identifier of a selector 810 that in response to user actuation or activation triggers communication an instruction to the system 100 to apply a filter (e.g., adaptive or non-adaptive, periodic 25.5 Hz, 12.5 Hz, 6 Hz, etc.) associated with the selector 810 to reduce or remove frequency component of the noise or otherwise condition the ECG waveform data received from the channel, lead or electrode 130, as described above in method 708. The display 800 can further include a graphic illustration of a selector switch 815 that when toggled can active or inactive application of a subtractive filter to condition ECG waveform data received from across all or selected channels, leads, or electrodes 130. The selectors 810 or 815 can be labeled with the particular bandwidth or central frequency or wavelength associated with the frequency component to be reduced or removed with application of a filter algorithm (e.g., adaptive or non-adaptive, static, subtractive, etc.) associated with the selectors 810, 815. The type and number of selectors 810, 815 and respective types of filters (e.g., adaptive and non-adaptive, subtraction, static, etc.) to be applied can vary. The selectors 810, 815 can be displayed in order of significance or color coded representative of an amount of reduction or removal of noise content (e.g., highest amplitude or frequency or bandwidth of noise to be reduced or removed) from the acquired ECG waveform data.

The display 800 can also include a graphic illustration of a vector 820 representative of direction and amplitude of the source of noise as detected by the system 100 in combination with the location tracking system 450 and ECG signal acquisition system 112. An embodiment of the graphic illustration 820 can include a detected direction of the source of the noise relative to a reference axis 822 of the defined space or subject 105, as shown by the arrows 830, 835, 840 representative of direction and amplitude of noise relative to the graphic illustration of the subject 105 on the display 800. The display 800 can include multiple graphic illustrations 830, 835, 840 of the direction and amplitude directed to detection of multiple sources of noise signals or attenuation (e.g., noise signals having different frequencies, continuous, periodic, or non-periodic characteristics). The display 800 can further include a graphic illustration of a comparison 842 of the measured parameters of the detected noise signals from different sources (e.g., different amplitudes, frequencies, wavelengths, periodic versus continuous, etc.) for visualization to the user.

The display 800 can further include a graphic illustration of the ECG waveform data 845 acquired for unique amplifier channels, leads, or electrodes 130 or combination thereof. Each graphic illustration 845 can be color coded, filled, or other unique graphic to further distinguish one from another. The display 800 can further include a graphic illustration of an alert 850 of the detection of the noise signal or attenuation by the system 100 having a threshold frequency or wavelength or amplitude. This graphic illustration of the alert 850 can be associated with an indication or graphic illustration of an automatic activation 855 of one of the adaptive or fixed filters in response to detection of the noise signal or attenuation having a threshold bandwidth, frequency or amplitude. The display 800 can further include yet another graphic illustration (e.g., color, graphic design such as cross-hatching or like) indicative of the detected electrode or channel 860 as the source of the noise signal within the range of bandwidth or frequency or wavelength threshold. The graphic illustration 860 can be color coded or have graphic design that correlates to the graphic illustration of one of the graphic illustrations of the ECG waveforms 845 (as shown in FIG. 13) correlated to the respective electrodes or channels 135 detected to be source or origination of the noise attenuation.

It should be understood that one or more the above-described features in each of the displays 400 and 800 can vary in number and can be included in combination with anyone of the other features described in the other of the displays 400 and 800 and is not limited on the subject matter described herein.

A technical effect of the above-described embodiments of the subject matter described above can include providing the system 100 and method to mimic an effect of, detect, and locate sources of noise related interference in an environment to perform electrical signal tracking and processing such as an electrophysiological study room where an ECG can be measured of the subject 105. The ability to detect and isolate a location of the source of noise interference in an ECG study environment can enhance procedural results, reduce the time to complete an ECG case study. The system 100 and method can also enhance the servicing, maintenance, and debugging poor performance of the ECG y recording systems 120.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to use in combination with an ECG signal acquisition system connected to an arrangement of electrodes on a subject, the system comprising:
    an antenna system in communication with the ECG signal acquisition system;
    a location tracking system operable to track a direction and a location of the antenna system relative to a reference; and
    an interface connected in communication with the ECG signal acquisition system and the location tracking system, the interface capable of producing an output indicative of a direction of a source of a noise signal detected by the antenna system, wherein a filter is operatively linked to the system and adapted to reduce an effect of the noise signal on an acquired ECG waveform data received by the ECG signal acquisition system.

2. The system of claim 1, wherein the system is configured to automatically identify the filter to reduce the effect of the noise signal on the acquired ECG waveform data received by the ECG signal acquisition system, wherein the interface includes a graphic illustration on a display of the identification of the filter to reduce the effect of the noise signal.

3. The system of claim 1, wherein the filter includes at least one adaptive filter defined by at least one coefficient to reduce an effect of noise signals at different frequencies, and wherein the system is configured to automatically calculates the at least one coefficient for each adaptive filter to reduce effects of different noise signals on the acquired ECG waveform data received by the ECG signal acquisition system.

4. The system of claim 1, wherein the system is configured to detect and generate a graphic illustration of a direction and an amplitude of a source of the noise signal for illustration on a display of the interface relative to the reference, and wherein the system is configured to automatically detects at least one electrode from the arrangement electrodes attached at the subject of closest proximity to the direction of the source of the noise signal.

5. The system of claim 4, wherein the system is configured to automatically selects the filter to be applied to the ECG waveform data acquired from the at least one electrode, but not to be applied to ECG waveform data acquired from a remainder of the electrodes that does not include the at least one electrode.

6. The system of claim 1, wherein the interface includes a display having a graphic illustration associated with a unique filter to reduce the effects of different noise signals on the ECG waveform data acquired from a plurality of electrodes from the arrangement of electrodes, and further including a graphic illustration of a classification of the noise having a graphic design of the graphic illustration of one of the filters calculated by the system to reduce the effects of the noise signal on the ECG waveform data.

7. The system of claim 1, wherein the interface includes a display having a graphic illustration indicative of selected electrodes from the plurality of electrodes that the system automatically selected to apply the filter to best reduce the effects of the noise signal on the acquisition of the ECG waveform data from the subject.

8. The system of claim 1, wherein the interface includes a display with a graphic illustration of an alert of detection of the noise signal by the system and a graphic illustration indicative an automatic application of the filter by the system to reduce the effects of the noise signal on the ECG waveform data acquired from the subject.

9. The system of claim 8, further including a graphic illustration of the ECG waveform data acquired from each electrode to enable a user to selectively view in real-time the ECG waveform data filtered by one or more filters.

10. The system of claim 1, wherein the system is configured to detect and generate a graphic illustration of a direction and an amplitude for each of a plurality of sources of noise signals for illustration on a display of the interface relative to a reference, each graphic illustration of direction and amplitude having a unique identifier such as a color or graphic design.

11. The system of claim 1, wherein the antenna system includes a circuit board having an alignment to define a direction relative to a reference with moving of the circuit board in a define space where the subject is located.

12. The system of claim 1, wherein the antenna system includes an unterminated input having a lead wire extending in a direction in general parallel alignment to a leg of the subject.

13. The system of claim 1, wherein the antenna system is embedded in a table in support of the patient.

* * * * *